(12) United States Patent
Chassaing

(10) Patent No.: US 7,893,271 B2
(45) Date of Patent: Feb. 22, 2011

(54) BENZIMIDAZOLE CARBAMATES AND (THIO) CARBAMATES, AND THE SYNTHESIS AND USE THEREOF

(75) Inventor: Christophe Pierre Alain Chassaing, Ingelheim am Rhein (DE)

(73) Assignee: Intervet International B.V., Boxmeer (NL)

( * ) Notice: Subject to any disclaimer, the term of this patent is extended or adjusted under 35 U.S.C. 154(b) by 496 days.

(21) Appl. No.: 11/997,057

(22) PCT Filed: Jul. 18, 2006

(86) PCT No.: PCT/EP2006/064381

§ 371 (c)(1),
(2), (4) Date: Jan. 28, 2008

(87) PCT Pub. No.: WO2007/014846

PCT Pub. Date: Feb. 8, 2007

(65) Prior Publication Data

US 2009/0131369 A1 May 21, 2009

Related U.S. Application Data

(60) Provisional application No. 60/703,370, filed on Jul. 28, 2005.

(30) Foreign Application Priority Data

Jul. 28, 2005 (EP) .................................. 05106991

(51) Int. Cl.
*A61K 31/675* (2006.01)
*C07F 9/06* (2006.01)
(52) U.S. Cl. ......................... 548/113; 514/81
(58) Field of Classification Search .................. 548/113
See application file for complete search history.

(56) References Cited

U.S. PATENT DOCUMENTS

| | | | |
|---|---|---|---|
| 3,480,642 | A | 11/1969 | Stedman |
| 3,574,845 | A | 4/1971 | Actor et al. |
| 3,657,267 | A | 4/1972 | van Gelder et al. |
| 3,891,758 | A | 6/1975 | Hannah |
| 3,915,986 | A | 10/1975 | Gyurik et al. |
| 3,929,821 | A | 12/1975 | Beard et al. |
| 3,954,791 | A | 5/1976 | Loewe et al. |
| 3,993,682 | A | 11/1976 | Kolling et al. |
| 4,406,893 | A | 9/1983 | Nafissi-Varchei |
| 4,639,463 | A | 1/1987 | Rosner et al. |
| 5,459,155 | A | 10/1995 | Banks |
| 6,093,734 | A | 7/2000 | Garst et al. |

FOREIGN PATENT DOCUMENTS

EP 1214052 B1 8/2004
WO 9312124 A1 6/1993

OTHER PUBLICATIONS

Dhaneshwar, S.R., et al., "Synthesis and anthelmintic activity of some mannich bases of fenbendazole and albendazole," Indian Drugs, 28(1), pp. 24-26 (1990).
Hernandez-Luis, F., et al., "Synthesis and hydrolytic stability studies of albendazole carrier prodrugs," Bioorganic & Medicinal Chemistry Letters, 11, pp. 1359-1362 (2001).
Klocking, H.P., et al., Uber die pharmakolgie des antifibrinolytikums p-aminomethylbenzoesaure, Haematologia, Suppl. 1, pp. 175-179 (1970).
McKellar, Q.A., et al., "The benzimidazole anthelmintic agents—a review," J. Vet. Pharmacol. Therap., 13, pp. 223-247 (1990).
Nielsen, L.S., "Improved peroral bioavailability of mebendazole in rabbits by administration of various N-alkoxycarbonyl derivatives of mebendazole," Int'l Journal of Pharamceutics, 104, pp. 175-179 (1994).

*Primary Examiner*—Laura L. Stockton
(74) *Attorney, Agent, or Firm*—TraskBritt, P.C.

(57) ABSTRACT

This invention relates to benzimidazole carbamates and (thio) carbamates corresponding to Formula I:

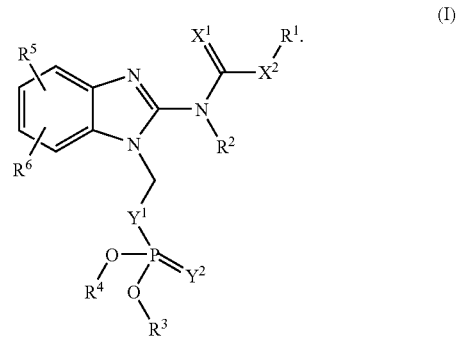

Here, $X^1$ and $X^2$ are independently O or S, wherein at least one of $X^1$ and $X^2$ is O; $Y^1$ and $Y^2$ are independently O or S, wherein at least one of $Y^1$ and $Y^2$ is O; $R^1$ is alkyl having from 1-4 carbon atoms; $R^2$, $R^3$, and $R^4$ are independently hydrogen or a cation; $R^5$ and $R^6$ are independently hydrogen, halogen, alkyl (having from 1-8 carbon atoms), $-OR^7$, $-SR^8$, $-CO-R^9$, $-OSO_2-Ar$, or $-S(O)R^{10}$; $R^7$ is alkyl having from 1-8 carbon atoms; $R^8$ is alkyl (having from 1-8 carbon atoms) or aryl; $R^9$ is alkyl (having from 1-8 carbon atoms), cycloalkyl (having from 3-6 carbon atoms), or aryl; Ar is aryl; and $R^{10}$ is alkyl (having from 1-8 carbon atoms) or aryl. The compounds generally are soluble and stable in water, and have antiparasitic (particularly anthelmintic) activity in vivo that is comparable to known water-insoluble benzimidazole carbamates (e.g., albendazole and fenbendazole).

24 Claims, No Drawings

US 7,893,271 B2

BENZIMIDAZOLE CARBAMATES AND (THIO) CARBAMATES, AND THE SYNTHESIS AND USE THEREOF

PRIORITY CLAIM TO RELATED PATENT APPLICATIONS

This patent claims priority under 35 U.S.C. §371 as a national phase of Int'l Patent Appl. No. PCT/EP2006/064381 (filed Jul. 18, 2006; and published Feb. 8, 2007 as Int'l Publ. No. WO2007/014846), which, in turn, claims priority to U.S. Provisional Patent Appl. No. 60/703,370 (filed Jul. 28, 2005) and Europe Patent Appl. No. 05106991.2 (filed Jul. 28, 2005). The entire text of each of the above-referenced patent applications is incorporated by referenced into this patent.

FIELD OF THE INVENTION

The present invention is concerned with novel benzimidazole carbamates and (thio)carbamates with antiparasitic activity.

BACKGROUND OF THE INVENTION

Benzimidazoles were originally developed as plant fungicides and later as veterinary and human anthelmintics. The family of benzimidazoles with anthelmintic activity includes thiazolyl benzimidazoles and benzimidazole carbamates. The benzimidazoles show a broad spectrum of activity against helminth parasites. Well known benzimidazoles with activity against helminths are for example thiabendazole; cambendazole; and benzimidazole carbamates, such as parbendazole (U.S. Pat. No. 3,480,642), mebendazole (U.S. Pat. No. 3,657,267), flubendazole (U.S. Pat. No. 3,657,267), fenbendazole (U.S. Pat. No. 3,954,791), oxfendazole (U.S. Pat. No. 3,929,821), oxibendazole (U.S. Pat. No. 3,574,845), albendazole (U.S. Pat. No. 3,915,986), ricobendazole (albendazole sulfoxide) (U.S. Pat. No. 3,915,986) and luxabendazole (U.S. Pat. No. 4,639,463), all of which differ in the substituents on the parent benzimidazole nucleus.

Benzimidazoles are believed to owe their activity to the fact that they block the polymerization of beta-tubulin into microtubules. This affects the transport functions of cells within the parasite and ultimately kills the parasite.

Phenylguanidine prodrugs that are metabolically transformed into anthelmintic benzimidazoles have also been developed. Febantel (U.S. Pat. No. 3,993,682), for example, is a prodrug that is converted into fenbendazole, and netobimin (U.S. Pat. No. 4,406,893) yields albendazole.

Benzimidazoles are generally poorly soluble in water. They are given per oral as a suspension, paste or powder, or by intraruminal injection (McKellar and Scott, J. Vet. Pharmacol. Therap., 13, 223-247, 1990). The fact that benzimidazoles, and especially benzimidazole carbamates, are poorly soluble in water limits their applications. In particular, the solubility of the benzimidazole carbamates is extremely low, probably due to the presence of the carbamate group on the benzimidazole moiety. These compounds are practically insoluble in water. For some useful applications of the compounds, such as the use in aquaculture applications and drinking water applications, the poor water solubility of the benzimidazoles is a major obstacle.

A lot of effort has already been put into solving the problem of poor- or non-aqueous solubility of benzimidazole(carbamate)s.

Attempts have also been made to provide more soluble derivatives of benzimidazoles (prodrugs, which are metabolized into the active compound). The efficacy of a prodrug depends on many factors, such as the rate and the extent to which the prodrug is converted into the active substance and the site of this transformation. Moreover the prodrug should possess high solubility in water at the pH of maximal stability, and sufficient aqueous stability prior to the application. Of course the prodrug should be well tolerated and should not be more toxic than the active compound.

Efforts regarding benzimidazole prodrugs were undertaken in the context of the use of the benzimidazoles in the combat of systemic infections, for example with the larval stage of the cestodes, *Echinococcus multicularis* and *E. granulosis*. In these cases plasma and tissue levels of the drugs are important since, in order to act systemically, the benzimidazoles have to be taken up into the bloodstream.

Certain albendazole prodrugs are described by Hernández-Luis et al. in Bioorganic & Medicinal Chemistry Letters, 11, 1359-1362, 2001. Hernández-Luis et al. attempted to enhance the solubility of albendazole by synthesizing three N-acyl and two N-alkoxycarbonyl derivatives. These derivatives were developed mainly in the context of the use of albendazole prodrugs for some tissue dwelling infestations such as trichinellosis, hydrated disease (echinococcsis) and neurocysticerosis, where high doses and long treatment are required due to the poor solubility and absorption of albendazole.

Another group, Nielsen et al. (Acta Pharm. Nord., 4(1), 43-49, 1992) made prodrugs of thiabendazole by N-acylation of the benzimidazole moiety with various chloroformates as well as by acylmethylation, also with the aim of improving solubility of the benzimidazoles for use against hydrated disease. One N-(4-amino-methylbenzoyl)oxymethyl derivative was reported to have a 300-fold increased water solubility. However, this type of compound is not particularly stable towards hydrolysis, and would therefore be unsuitable, for example, for drinking water applications. Its solubility is also still insufficient to be used in drinking water applications. Moreover, it should be noted that 4-aminomethylbenzoic acid has been used as an antibrinolytic agent (Kloecking, H. P.; Markwardt, F., Haematologia, Supplement 1, 175-9, 1970), suggesting that the cleaved pro-moiety is not pharmacologically inactive. The Nielsen group also reported N-alkoxycarbonyl derivatives of mebendazole in Int. J. Pharm., 104,175-179, 1994.

Mannich bases of albendazole and fenbendazole were prepared by Dhaneshwar et al., Indian drugs, 28(1), 24-26, 1990, using various secondary amines such as dimethylamine, dipropylamine, pyrrolidine, piperazine, etc. Further Mannich bases are described in Garst et al. (U.S. Pat. No. 6,093,734). However, actual activity has not been demonstrated for the Mannich bases, and these derivative show very low stability in water.

A water soluble prodrug of albendazole exists, namely netobimin. But although netobimin is water soluble, it has been reported to cause embryonal toxicity.

In WO9312124 another class of benzimidazoles is discussed, namely substituted 2-[[(3,4-dialkoxy-2-pyridinyl)-methyl]sulfonyl]-1(H)-benzimidazole-1-yl compounds. These benzimidazoles are gastric acid secretion inhibitors (proton pump inhibitors) and structurally resemble well-known gastric acid secretion inhibitors like omeprazole and lansoprazole. In contrast to the benzimidazole carbamates, which are practically insoluble in water, the benzimidazole proton pump inhibitors are markedly more soluble in water. For example, omeprazole has a solubility of 500 μg/mL In WO9312124 derivatives of these proton pump inhibitors are listed that are modified to contain a phosphonooxymethyl group attached as an N-substituent in position 1 on the benzimidazole nucleus. The thus modified compounds have the beneficial effect that they do not block the uptake of iodine into the thyroid gland. Furthermore the compounds are said to have a high solubility and chemical stability in water. It is believed that these compounds are metabolized at the N-substituent in position 1 of the benzimidazole nucleus before exerting their effect, which in effect makes them prodrugs. A syrup for oral administration of the compounds containing 1 g/L was prepared, as well as a solution for intravenous administration containing 4 mg/mL and 6 mg/mL.

Anthelmintic benzimidazole carbamates such as fenbendazole have much lower solubilities, being even lower than 0.05 μg/mL (Nguomo, A. J. PhD. Thesis, 1983, cited by McKellar et al. in J. Vet. Pharmacol. Therap. 1990, 13, 223-247).

Since benzimidazole carbamates are administered to, for example, poultry and pigs at large production farms, it would be convenient if the compounds could be administered via medicated drinking water. However, due to their very low solubility, administration via drinking water is highly problematic.

For drinking water applications, a lot of effort has been put into finding a suitable formulation for the compounds that assures accurate dosing. The problem with suspensions and emulsions of water insoluble drugs is that, in order to assure accurate dosing via a drinking water system, the suspension or emulsion must be uniform and very stable. EP1214052, for example, is concerned with a suspoemulsion for flubendazole, which is intended for use in drinking water applications.

Rather than preparing a suspension or emulsion, it would be more convenient if water soluble alternatives could be provided, for example, modified derivatives of the original, non-soluble active compounds, that still have the desired activity, or are converted in vivo to the actual active substances. But especially drinking water applications demand a very high solubility. For a drinking water application of any drug, usually a concentrate needs to be produced first, which requires even higher solubility of the drug. The compound should also dissolve in a short period of time. Moreover, if any compound which is to be administered via drinking water does not dissolve properly, or settles after a while, it may deposit in the pipes of a drinking water system, and the whole system may get clogged.

Because the drinking water may stand in the tanks or pipes of a drinking water system for a prolonged period of time, the compounds that are dissolved also need to be chemically very stable. If the compounds are not chemically stable over a prolonged period of time, none, or an insufficient quantity, of the actual active compound may reach the animals drinking the water. Especially for drinking water applications, a stability of at least 8 hours at a pH range from 5 to 9 is required.

A guideline on "quality aspects of pharmaceutical veterinary medicines for administration via drinking water" (EMEA/CVMP/540/03) was published by the European Medicines Agency (EMEA). In this guideline quality data requirements are reflected for veterinary medicinal products that are administered in drinking water to animals. The guideline provides, for example, criteria for the stability and solubility of the products and the time taken for them to fully dissolve.

Thus, especially for drugs that are to be administered via drinking water systems, such as those used at large animal production facilities, there are a lot of constraints that limit the suitability of many drugs, and especially benzimidazole carbamates, for this particular purpose.

BRIEF SUMMARY OF THE INVENTION

The present invention provides new benzimidazole carbamates and (thio)carbamates that dissolve readily in water, are chemically stable, and provide excellent antiparasitic activity. The compounds according to the invention are suitable for the same therapeutic applications as state of the art benzimidazole carbamates, and are especially suitable for use as anthelmintics.

Briefly, this invention is directed, in part, to compounds corresponding to Formula I:

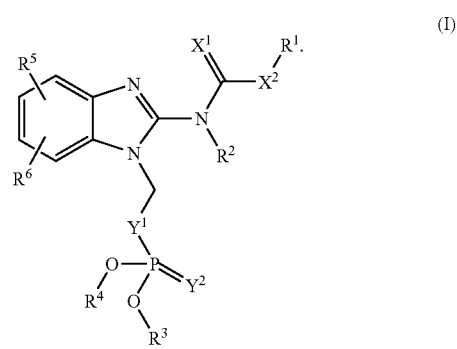

Here:
  $X^1$ and $X^2$ are independently O or S, wherein at least one of $X^1$ and $X^2$ is O;
  $Y^1$ and $Y^2$ are independently O or S, wherein at least one of $Y^1$ and $Y^2$ is O;
  $R^1$ is alkyl having from 1-4 carbon atoms;
  $R^2$, $R^3$, and $R^4$ are independently hydrogen or a cation;
  $R^5$ and $R^6$ are independently hydrogen, halogen, alkyl (having from 1-8 carbon atoms), —$OR^7$, —$SR^8$, —CO—$R^9$, —$OSO_2$—Ar, or —$S(O)R^{10}$;
  $R^7$ is alkyl having from 1-8 carbon atoms;
  $R^8$ is alkyl (having from 1-8 carbon atoms) or aryl;
  $R^9$ is alkyl (having from 1-8 carbon atoms), cycloalkyl (having from 3-6 carbon atoms), or aryl;
  Ar is aryl; and
  $R^{10}$ is alkyl (having from 1-8 carbon atoms) or aryl.

This invention also is directed, in part, to pharmaceutical compositions comprising at least one compound discussed above, and at least one pharmaceutically acceptable carrier.

This invention also is directed, in part, to a method for treating an animal against a parasite. The method comprises administering at least one of the compounds discussed above to the animal.

This invention also is directed, in part, to a method for treating an animal against a helminth. The method comprises administering at least one of the compounds discussed above to the animal.

DETAILED DESCRIPTION OF PREFERRED EMBODIMENTS

The present invention provides compounds of the following general formula I:

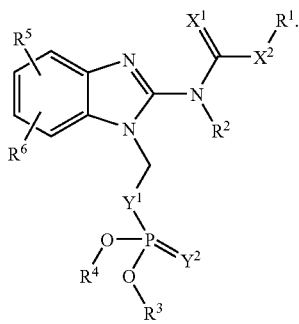

Formula I

Here:

$X^1$ and $X^2$ are either S or O. Preferably, at least one of the two is O, and most preferably both are O.

$Y^1$ and $Y^2$ are either S or O. Preferably, at least one of the two is O, and most preferably both are O.

Preferred compounds according to the invention are N-phosphonooxymethyl substituted benzimidazole carbamates that fit the general formula I, i.e., compounds in which $X^1$, $X^2$, $Y^1$, and $Y^2$ are O.

$R^1$ is alkyl having 1-4 carbon atoms, preferably methyl.

$R^2$, $R^3$, and $R^4$ are independently of each other hydrogen or a cation. Preferably, the cation is sodium, potassium, or ammonium. Preferred compounds according to the invention are salts, i.e., compounds wherein one or more of $R^2$, $R^3$, and $R^4$ are cations. This includes salts wherein, for example, $R^2$ is H, and $R^3$ and $R^4$ are sodium. It also includes salts wherein all three of $R^2$, $R^3$, and $R^4$ are sodium. And it includes mixtures of, for example, di- and tri-sodium salts.

$R^5$ and $R^6$ are both independently hydrogen, halogen, alkyl, —$OR^7$, —$SR^8$, —CO—$R^9$, —$OSO_2$—Ar, or —S(O)$R^{10}$. When $R^5$ and/or $R^6$ are alkyl, they have 1-8 carbon atoms, preferably 1-6 carbon atoms, and most preferably 4 carbon atoms, wherein the most preferred compounds are (5- and 6-butyl-1-phosphonooxymethyl-1(H)-benzoimidazol-2-yl)-carbamic acid methyl esters (e.g., N-phosphonooxymethyl substituted parbendazole) or a mixture thereof, and most preferably salts thereof.

$R^7$ is alkyl or aryl. The alkyl has 1-8 carbon atoms, preferably 1-6 carbon atoms, and most preferably 3 carbon atoms, wherein preferred compounds are (1-phosphonooxymethyl-5- and 6-propoxy-1(H)-benzoimidazol-2-yl)-carbamic acid methyl esters (e.g., N-phosphonooxymethyl substituted oxibendazole) or a mixture thereof, and most preferably salts thereof. When $R^7$ is an aryl, it preferably is a phenyl group which may be substituted or unsubstituted.

$R^8$ is alkyl or aryl. The alkyl has 1-8 carbon atoms, preferably 1-6 carbon atoms, and most preferably 3 carbon atoms, wherein the most preferred compounds are (1-phosphonooxymethyl-5- and 6-propylsulfanyl-1(H)-benzoimidazol-2-yl)-carbamic acid methyl esters (e.g., N-phosphonooxymethyl substituted albendazole) or a mixture thereof, and most preferably salts thereof. When $R^8$ is aryl, it preferably is a phenyl group which may be substituted or unsubstituted, wherein preferred compounds are (5- and 6-phenylsulfanyl-1-phosphonooxymethyl-1(H)-benzoimidazol-2-yl)-carbamic acid methyl esters (e.g., N-phosphonooxymethyl substituted fenbendazole) or a mixture thereof, and most preferably salts thereof.

$R^9$ is alkyl, cycloalkyl, or aryl. The alkyl has 1-8 carbon atoms. The cycloalkyl has 3-6 carbon atoms, wherein the most preferred compounds are (5- and 6-cyclopropanecarbonyl-1-phosphonooxymethyl-1(H)-benzoimidazol-2-yl)-carbamic acid methyl esters (e.g., N-phosphonooxymethyl substituted ciclobendazole) or a mixture thereof, and most preferably salts thereof. When $R^9$ is aryl, it is preferably a substituted or unsubstituted phenyl group, whereby preferred compounds are (5- and 6-benzoyl-1-phosphonooxymethyl-1(H)-benzoimidazol-2-yl)-carbamic acid methyl esters (e.g., N-phosphonooxymethyl substituted mebendazole) or a mixture thereof, and most preferably salts thereof. When the phenyl group is substituted, halo substituents such as fluorine are preferred, which can be in the para position, and preferred compounds are [5- and 6-(4-fluorobenzoyl)-1-phosphonooxymethyl-1(H)-benzoimidazol-2-yl]-carbamic acid methyl esters (e.g., N-phosphonooxymethyl substituted flubendazole) or a mixture thereof, and most preferably salts thereof.

Ar is aryl. Preferably, Ar is a substituted or unsubstituted phenyl group. When the phenyl is substituted, it preferably is substituted in the position 4 by a fluorine atom, wherein the most preferred compounds are 4-fluorobenzenesulfonic acid 2-methoxycarbonylamino-1-phosphonooxymethyl-1(H)-benzoimidazol-5- and 6-yl esters (e.g., N-phosphonooxymethyl substituted luxabendazole) or a mixture thereof, and most preferably salts thereof.

$R^{10}$ is alkyl or aryl. The alkyl has from 1-8 carbon atoms, preferably 3 carbon atoms, wherein preferred compounds are [1-phosphonooxymethyl-5- and 6-(propane-1-sulfinyl)-1(H)-benzoimidazol-2-yl]-carbamic acid methyl esters (e.g., N-phosphonooxymethyl substituted ricobendazole) or a mixture thereof and most preferably salts thereof. When $R^{10}$ is aryl, it preferably is a substituted or unsubstituted phenyl group, and preferred compounds are (5- and 6-benzenesulfinyl-1-phosphonooxymethyl-1(H)-benzoimidazol-2-yl)-carbamic acid methyl esters (e.g., N-phosphonooxymethyl substituted oxfendazole) or a mixture thereof, and most preferably salts thereof.

Preferably $R^5$ is H and $R^6$ is attached to the 5- or 6-position of the benzimidazole nucleus.

Alkyl groups may be straight or branched, for example methyl, ethyl, n-propyl, isopropyl, butyl, sec-butyl, tert-butyl, hexyl and octyl, and may optionally be substituted, for example with a halo substituent. In preferred compounds of the invention containing an alkyl, the alkyl is a straight chain and non-substituted. The term aryl means an aromatic hydrocarbon group having 6-14 carbon atoms, such as phenyl, naphthyl, which may optionally be substituted with one or more substituents, such as hydroxy, halogen, nitro, cyano, amino, alkyl, alkoxy, amino as long as it doesn't affect the affect the antiparasitic activity of the compound. In preferred compounds of the invention containing a phenyl group, said phenyl is non-substituted or substituted with a halo substituent.

Some of the compounds within the above described general formula according to the invention, may, as a result of the synthetic route chosen, exist as a mixture of regioisomers. For example, a mixture of compounds may be synthesized wherein $R^6$ is attached to the 5-position on the benzimidazole nucleus and the 6-position on the benzimidazole nucleus, respectively. Besides the pure regioisomers, of course such mixtures comprising different regioisomers are likewise understood to be part of the present invention. Some of the compounds according to the invention may contain one or more chiral centres, forming optically active enantiomers. The general formula (Formula I) is intended to include the individual enantiomers as well as mixtures of enantiomers.

The compounds of the invention are highly soluble and stable in water. For example, a mixture of (5- and 6-phenylsulfanyl-1-phosphonooxymethyl-1(H)-benzoimidazol-2-yl)-carbamic acid methyl esters di-sodium salts has a solubility in water of 132 mM (67 g/L). Furthermore, other compounds according to the invention such as N-phosphonooxymethyl substituted albendazole, mebendazole, flubendazole and luxabendazole sodium salts have aqueous solubilities of at least 50 mM.

Moreover, it has been found that the compounds according to the invention are stable for over 8 hours at pH 5 and at pH 9, which are the lower and upper pH limits at which compounds should be stable for over 8 hours in order to be suitable for drinking water application.

Moreover the compounds of the present invention have excellent antiparasitic, and especially anthelmintic activity in vivo, which is comparable to the state of the art, water insoluble, benzimidazole carbamates such as albendazole and fenbendazole.

The compounds of the invention are thus especially useful for administration via medicated water to humans and animals, both food-producing animals (for example cattle, pigs, poultry or fish), as well as companion animals. Administration of medicated water is common practice in treating poultry and pigs housed on large production farms. But also for administration to individual animals, administration via medicated water may be suitable. The compounds of the invention are especially useful as anthelmintics. The present invention therefore enables the administration of anthelmintic benzimidazoles via medicated water.

Although the compounds according to the invention are especially suitable for administration via medicated water due to their high solubility, they may likewise be administered via any other suitable route, oral or otherwise, for example by injection. When administered orally, the compounds can also be mixed through feedstuff, or formulated into a pill, capsule, bolus or otherwise. While, for compounds according to the invention, oral administration routes are preferred, treatment via other routes of administration, for example parenteral, is also possible. For example, for pets, subcutaneous or intramuscular administration may also be possible.

The compounds may be used alone or in formulations adjusted for the specific use and to the specific parasites or host involved. The compounds according to the invention may be used alone, as the only active ingredient in a formulation, or together with other therapeutic agents.

The formulation and the route of administration will depend on the disease and on the method of treatment. Such formulations may be prepared in a standard manner in accordance with conventional veterinary or human medicinal practices. The present invention further encompasses a pharmaceutical composition comprising an effective amount of one or more compound(s) according to the invention.

Such compositions may further contain any necessary pharmaceutically acceptable auxiliaries, such as a carrier, stabilizer or other excipients, and optionally other therapeutic agents. The term "acceptable" means being compatible with the other ingredients of the composition and not deleterious to the recipients thereof.

A carrier may be a liquid diluent or a solid. Any conventional pharmaceutical carrier that does not interfere with the performance of the active ingredient can be used in the preparations according to the present invention.

Soluble drugs to be administered via drinking water may be supplied as granule or powder for solution or as a pre-concentrate for oral solution.

Formulations intended for oral use may contain flavouring agents, colouring agents, preserving agents and the like. Capsules, boluses and tablets may be prepared by mixing the active compound(s)/substance with a pharmaceutically acceptable diluent or carrier.

For parenteral administration, the compound may be dissolved or dispersed in a liquid carrier vehicle. Isotonic saline solutions and sterile injectable solutions may be used, containing pharmaceutically acceptable stabilizing agents. If necessary a preservative may be added.

The effective quantity or concentration of the compounds of the invention may vary and is dependent on individual needs. The minimum quantity is dependent on the desirable effect and the maximum is determined by undesired side effects. The actual dose used depends on the type and severity of infection. The specific dose level is influenced by many factors such as the activity of the compound employed, and the species, age, body weight, general health, diet, time of administration, route of administration, etc.

The compounds of the present invention can be prepared by following the synthetic sequence described below:

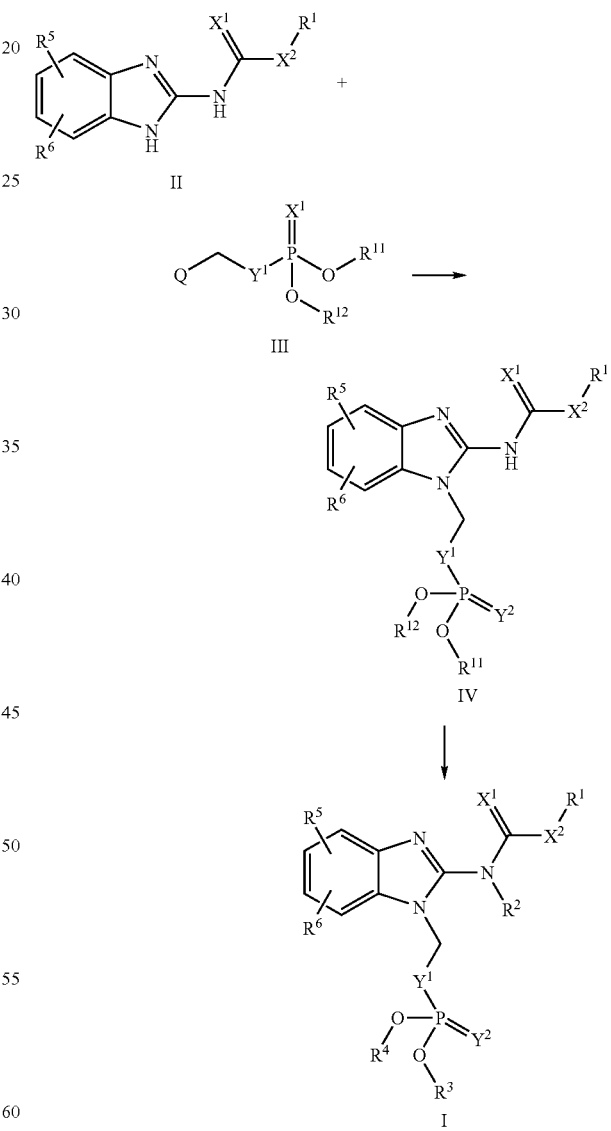

In the first step, a suitable salt of a functionalized benzimidazole carbamate or (thio)carbamate II such as a sodium, potassium or lithium salt, is reacted with a phosphoric acid diester III substituted with a methylene group bearing a leaving group, Q, such as chlorine, bromine, iodine, tosylate or mesylate, to afford a compound of formula IV, wherein $R^{11}$ and $R^{12}$ are protecting groups. Suitable protecting groups are known to a person skilled in the art, and can for example be alkyl such as tert-butyl, or phenyl or benzyl. This type of phosphate III can be prepared using literature procedures (e.g. Tetrahedron Letters; 2002, 43, 3793). The formation of the benzimidazole carbamate or (thio)carbamate alkali salt can be achieved by the addition of a base such as sodium hydroxide, potassium hydroxide, sodium hydride or potassium hydride to the benzimidazole carbamate or (thio)carbamate II at a temperature ranging between −10 and 30° C., in a suitable solvent, preferably an organic solvent, for example N,N-dimethylformamide, N,N-dimethylacetamide, N-methylpyrrolidone, N-ethylpyrrolidine, tetrahydrofuran or dioxane. The reaction of the salt thus obtained with the phosphate triester III can be performed at temperatures ranging from 0 to 80° C., preferably between 10 to 50° C. Depending on the temperature at which the reaction is performed, the reaction time may vary between 1 to 24 hours. Depending on the type of benzimidazole carbamate or (thio)carbamate reacted, the electrophile should be added to the nucleophile, or the addition should be achieved the other way around.

In the second step, the intermediates IV can then be hydrolysed to give compounds I (in which $R^2$, $R^3$ and $R^4$ are all H) by the addition of an acid, such as acetic acid, trifluoroacetic acid or hydrochloric acid, optionally in an organic solvent, such as diethyl ether, tetrahydrofuran, dioxane or dichloromethane at a temperature between room temperature and 50° C.

In an optional third step, the isolated products can then be converted into their corresponding salts I (in which at least one of $R^2$, $R^3$ and $R^4$ is a cation, preferably sodium, potassium or ammonium) by the addition of a base, such as sodium alkoxide, sodium hydroxide, potassium alkoxide, potassium hydroxide or ammonia. The reaction may be performed in water or in an organic solvent, such as methanol, ethanol, isopropanol, tert-butanol or mixtures thereof.

EXAMPLES

Example 1

Synthesis of (5-phenylsulfanyl-1-phosphonooxymethyl-1(H)-benzoimidazol-2-yl)-carbamic acid methyl ester di-sodium salt 6 and (6-phenylsulfanyl-1-phosphonooxymethyl-1(H)-benzoimidazol-2-yl)-carbamic acid methyl ester di-sodium salt 7

The compounds may be synthesized using the following general synthetic sequence:

STEP A: Synthesis of phosphoric acid di-tert-butyl ester chloromethyl ester 1

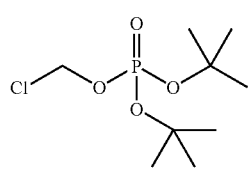

1

According to a literature procedure (Tetrahedron Letters; 2002, 43, 3793), compound I was prepared as follows: Potassium di-tert-butyl phosphate (6.35 g), tetra-n-butylammonium hydrogen sulphate (917 mg) and sodium bicarbonate (8.96 g) were dissolved in water (230 mL). Dichloromethane was added (130 mL) and the resulting mixture was cooled down to 0° C. A solution of chloromethylchlorosulphate (917 mg) in dichloromethane (100 mL) was slowly added under vigorous stirring. The reaction mixture was allowed to reach room temperature and further stirred overnight at this temperature. The organic layer was then separated, washed with brine (50 mL), dried over $Na_2SO_4$ and concentrated under vacuum. The desired product 1 was obtained as a colourless oil (2.4 g). Phosphoric acid di-tert-butyl ester chloromethyl ester 1. Colourless oil, $^1$H-NMR (CDCl$_3$) δ 5.65 (d, J=15.0 Hz, 2H), 1.52 (s, 18H); $^{13}$C-NMR (CDCl$_3$) δ 84.2 (d, J=7.6 Hz), 73.3 (d, J=6.9 Hz), 29.8 (d, J=4.3 Hz); $^{31}$P-NMR (CDCl$_3$) δ −11.8.

STEP B: Synthesis of [1-(di-tert-butoxy-phosphonooxymethyl)-5-phenylsulfanyl-1(H)-benzo-imidazol-2-yl]-carbamic acid methyl ester 2 and [1-(di-tert-butoxy-phosphonooxymethyl)-6-phenylsulfanyl-1(H)-benzoimidazol-2-yl]-carbamic acid methyl ester 3

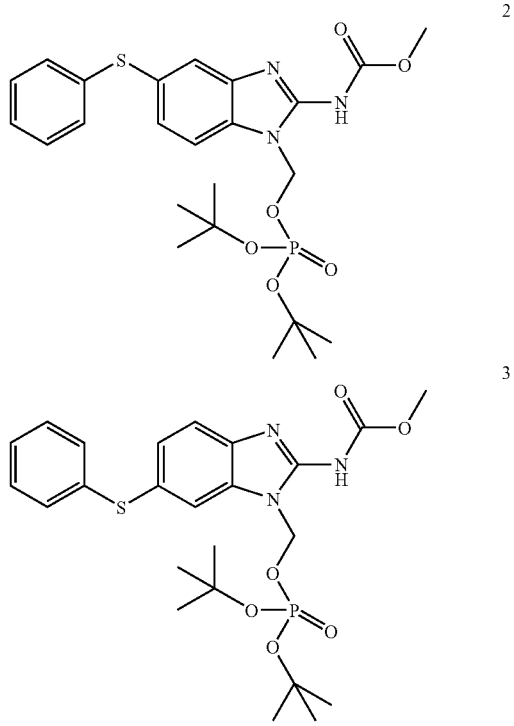

(5-Phenylsulfanyl-1(H)-benzoimidazol-2-yl)-carbamic acid methyl ester (2 g) was dissolved in dimethylformamide (200 mL), and a sodium hydride 60% suspension in mineral oil (960 mg) was added. The resulting green solution was stirred for 45 min at room temperature and a solution of phosphoric acid di-tert-butyl ester chloromethyl ester (2.3 g) in dimethylformamide (100 mL) was slowly added. The reaction was stirred at room temperature for 5 hours. The mixture was then diluted with dichloromethane (600 mL). The organic phase was then sequentially washed with water (300 ml), aqueous saturated NaHCO$_3$ (300 mL) and brine (two times 200 mL), dried over Na$_2$SO$_4$, and filtered. The organic layer was cooled to 4° C., the precipitated unreacted (5-phenylsulfanyl-1(H)-benzoimidazol-2-yl)-carbamic acid methyl ester was filtered off and the filtrate concentrated under vacuum. The oily residue was purified by filtration on a short pad of silica gel. The non-polar contaminants were eluted with ethyl acetate/petroleum ether 1:1 and the desired product was then eluted with diethyl ether. The desired product was obtained as a colourless solid (1.4 g), in a 1:1 ratio of the two regio-isomers 2 and 3. [1-(Di-tert-butoxy-phosphonooxymethyl)-5-phenylsulfanyl-1(H)-benzoimidazol-2-yl]-carbamic acid methyl ester 2. Colourless solid, $^1$H-NMR (DMSO-$d_6$) δ 12.2 (s, 1H), 7.49 (d, J=8.4 Hz, 1H), 7.47 (s, 1H), 7.34 (d, J=8.1 Hz, 1H), 7.33 (t, J=7.3 Hz, 2H), 7.24 (t, J=7.2 Hz, 1H), 7.19 (d, J=7.3 Hz, 2H), 5.85 (d, J=10.3 Hz, 2H), 3.64 (s, 3H), 1.34 (s, 18H); $^{13}$C-NMR (DMSO-$d_6$) δ 162.8, 154.1, 137.3, 130.8, 129.9, 129.2, 127.9, 127.6, 127.1, 116.1, 111.6, 83.1 (d, J=7.2 Hz), 67.0, 52.5, 29.7 (d, J=3.9 Hz); $^{31}$P NMR (DMSO-$d_6$) δ −11.3 (t, J=10.3 Hz). [1-(Di-tert-butoxy-phosphonooxymethyl)-6-phenylsulfanyl-1(H)-benzoimidazol-2-yl]-carbamic acid methyl ester 3. Colourless solid, $^1$H-NMR (DMSO-$d_6$) δ 12.3 (s, 1H), 7.60 (s, 1H), 7.46 (d, 1H), 7.32 (d, 1H), 7.30 (t, 2H), 7.21 (t, 1H), 7.19 (d, 2H), 5.83 (d, J=10.2 Hz, 2H), 3.63 (s, 3H), 1.30 (s, 18H); $^{13}$C-NMR (DMSO-$d_6$) δ 162.8, 154.1, 137.6, 130.2, 129.9, 129.8, 129.3, 128.6, 126.8, 126.4, 113.1, 115.5, 83.1 (d, J=7.2 Hz), 67.0, 52.5, 29.6 (d, J=3.9 Hz); $^{31}$P-NMR (DMSO-$d_6$) δ −11.4 (t, J=10.2 Hz).

STEP C: Synthesis of (5-phenylsulfanyl-1-phosphonooxymethyl-1(H)-benzoimidazol-2-yl)-carbamic acid methyl ester 4 and (6-phenylsulfanyl-1-phosphonooxymethyl-1(H)-benzoimidazol-2-yl)-carbamic acid methyl ester 5

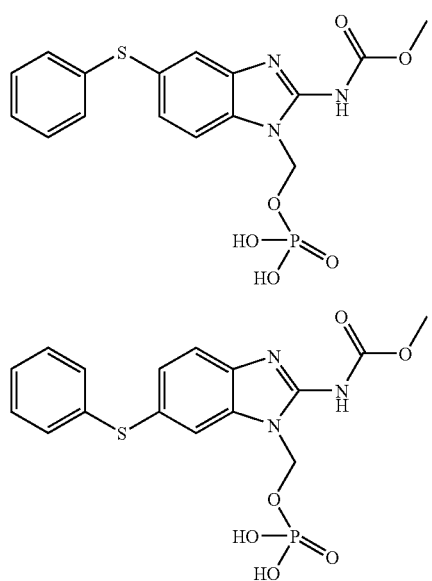

A 1:1 mixture of isomers 2 and 3 (1 g) was dissolved in dioxane (10 mL) and a 4N HCl solution in dioxane (10 mL) was added under stirring. The complete conversion of the starting materials into the corresponding acids was ensured by HPLC monitoring of the reaction. The precipitate formed was filtered off (550 mg) and the mother liquor concentrated under vacuum to half of the volume. Diethyl ether (5 mL) was added and a second crop of desired products (100 mg) was obtained after filtration. The desired products were obtained as a colourless solid (650 mg), in a 1:1 ratio of the two regio-isomers 4 and 5. (5-Phenylsulfanyl-1-phosphonooxymethyl-1(H)-benzoimidazol-2-yl)-carbamic acid methyl ester 4. $^1$H-NMR (D$_2$O) 87.41 (d, J=1.4 Hz, 1H), 7.39 (d, J=8.2 Hz, 1H), 7.15-7.07 (m, 6H), 5.52 (d, J=3.3 Hz, 2H), 3.53 (s, 3H); $^{13}$C-NMR (D$_2$O) δ 162.8, 158.6, 142.2, 137.9, 133.3, 129.3, 129.2, 128.3, 126.2, 124.3, 120.6, 110.2, 66.0, 52.1; $^{31}$P-NMR (D$_2$O) δ 1.97 (t, J=3.3 Hz). (6-Phenylsulfanyl-1-phosphonooxymethyl-1(H)-benzoimidazol-2-yl)-carbamic acid methyl ester 5. $^1$H-NMR (D$_2$O) δ 7.62 (d, J=1.4 Hz, 1H), 7.31 (d, J=8.2 Hz, 1H), 7.22-7.11 (m, 6I), 5.52 (d, J=4.3 Hz, 2H), 3.60 (s, 3H); $^{13}$C-NMR (D$_2$O) δ 161.4, 156.2, 139.8, 137.8, 133.2, 129.3, 128.6, 128.5, 128.1, 124.4, 114.7, 66.5, 52.3; $^{31}$P-NMR (D$_2$O) δ 2.24 (t, J=4.3 Hz).

STEP D: Synthesis of (5-phenylsulfanyl-1-phosphonooxymethyl-1(H)-benzoimidazol-2-yl)-carbamic acid methyl ester di-sodium salt 6 and (6-phenylsulfanyl-1-phosphonooxymethyl-1(H)-benzoimidazol-2-yl)-carbamic acid methyl ester di-sodium salt 7

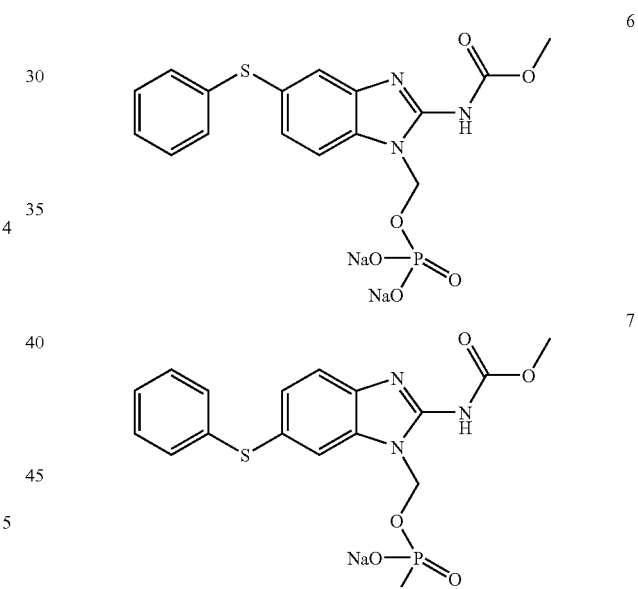

A 1:1 mixture of isomers 4 and 5 (50 mg) was suspended in methanol (2 mL) and a 0.1 N solution of sodium methoxide was added under stirring until pH 11 is reached. The solution was concentrated and then dried under high vacuum. The desired products were obtained (52 mg) as a white solid, in a 1:1 ratio of the two regio-isomers 6 and 7. (5-Phenylsulfanyl-1-phosphonooxymethyl-1(H)-benzoimidazol-2-yl)-carbamic acid methyl ester di-sodium salt 6 and (6-phenylsulfanyl-1-phosphonooxymethyl-1(H)-benzoimidazol-2-yl)-carbamic acid methyl ester di-sodium salt 7. $^1$H-NMR (D$_2$O) δ 7.75 (d, J=1.3 Hz, 1H), 7.59 (d, J=6.8 Hz, 1H), 7.58 (s, 1H), 7.46 (d, J=8.4 Hz, 1H), 7.40-7.26 (m, 12H), 5.69 (d, J=6.0 Hz, 2H), 5.66 (d, J=6.2 Hz, 2H), 3.76 (s, 3H), 3.75 (s, 3H); $^{31}$P-NMR (D$_2$O) δ 2.89 (s).

Example 2

Synthesis of (5-benzoyl-1-phosphonooxymethyl-1(H)-benzoimidazol-2-yl)-carbamic acid methyl ester di-sodium salt 8 and (6-benzoyl-1-phosphonooxymethyl-1(H)-benzoimidazol-2-yl)-carbamic acid methyl ester di-sodium salt 9

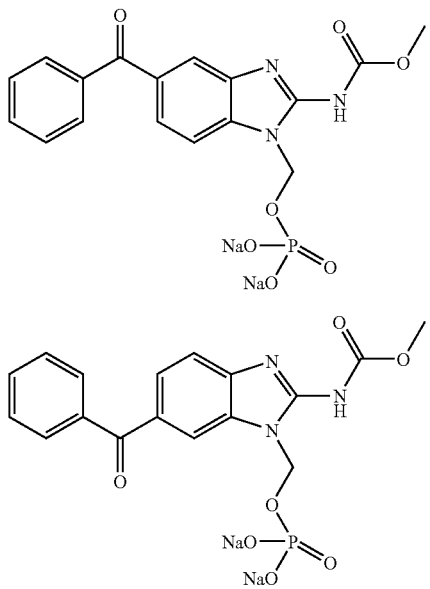

8

9

The compounds 8 and 9 were synthesised by using the synthetic sequence described in Example 1. (5-Benzoyl-1-phosphonooxymethyl-1(H)-benzoimidazol-2-yl)-carbamic acid methyl ester di-sodium salt 8 and (6-benzoyl-1-phosphonooxymethyl-1(H)-benzoimidazol-2-yl)-carbamic acid methyl ester di-sodium salt 9. $^1$H-NMR (D$_2$O) δ 7.91-7.45 (m, 16H), 5.67-5.61 (m, 4H), 3.73-3.71 (m, 6H); $^{31}$P-NMR (D$_2$O) δ 2.72 (s).

Example 3

Synthesis of 3-fluoro-benzenesulfonic acid 2-methoxycarbonylamino-1-phosphonooxymethyl-3(H)-benzoimidazol-5-yl ester di-sodium salt 10 and 3-fluoro-benzenesulfonic acid 2-methoxycarbonylamino-3-phosphono oxymethyl-3H-benzoimidazol-5-yl ester di-sodium salt 11

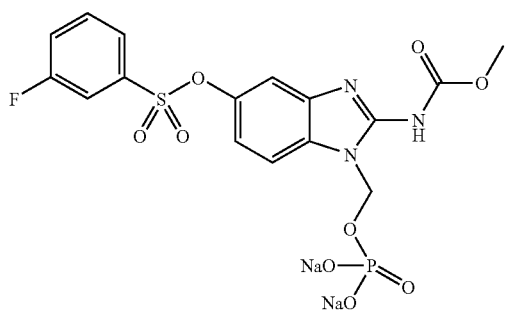

10

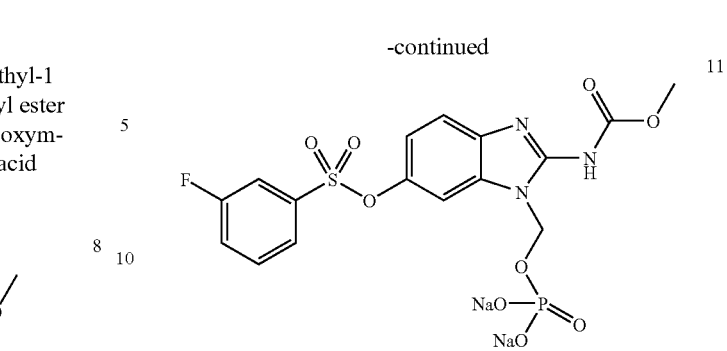

11

The compounds 10 and 11 were synthesised by using the synthetic sequence described in Example 1. 3-Fluoro-benzenesulfonic acid 2-methoxycarbonylamino-1-phosphonooxymethyl-3(H)-benzoimidazol-5-yl ester di-sodium salt 10 and 3-fluoro-benzenesulfonic acid 2-methoxycarbonylamino-3-phosphonooxymethyl-3(H)-benzoimidazol-5-yl ester di-sodium salt 11. $^1$H-NMR (D$_2$O) δ 7.83-7.75 (m, 4H), 7.39-7.20 (m, 8H), 6.80-6.70 (m, 2H), 5.58-5.61 (m, 4H), 3.71 (s, 6H); $^{31}$P-NMR (D$_2$O) δ 3.23 (s).

Example 4

Synthesis of (5-(4-fluoro)-benzoyl-1-phosphonooxymethyl-1(H)-benzoimidazol-2-yl)-carbamic acid methyl ester di-sodium salt 12 and (6-(4-fluoro)-benzoyl-1-phosphonooxymethyl-1(H)-benzoimidazol-2-yl)-carbamic acid methyl ester di-sodium salt 13

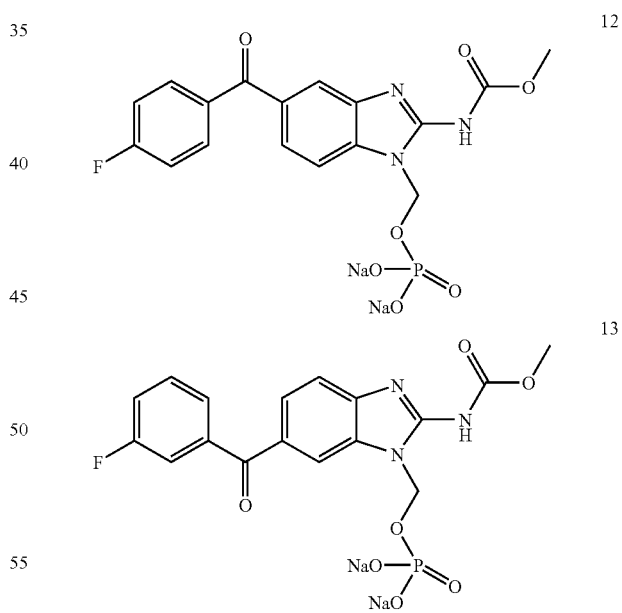

12

13

The compounds 12 and 13 were synthesised by using the synthetic sequence described in Example 1. (5-(4-Fluoro)-benzoyl-1-phosphonooxymethyl-1(H)-benzoimidazol-2-yl)-carbamic acid methyl ester di-sodium salt 12 and (6-(4-fluoro)-benzoyl-1-phosphonooxymethyl-1(H)-benzoimidazol-2-yl)-carbamic acid methyl ester di-sodium salt 13. $^1$H-NMR (D$_2$O) δ 7.86-7.45 (m, 10H), 7.21-7.16 (m, 4H), 5.66-5.60 (m, 4H), 3.71 (m, 6H); $^{31}$P-NMR (D$_2$O) δ 3.08 (s).

Example 5

Synthesis of 1-phosphonooxymethyl-5-propylsulfanyl-1(H)-benzoimidazol-2-yl)-carbamic acid methyl ester di-sodium salt 14 and 1-phosphonooxymethyl-6-propylsulfanyl-1(H)-benzoimidazol-2-yl)-carbamic acid methyl ester di-sodium salt 15

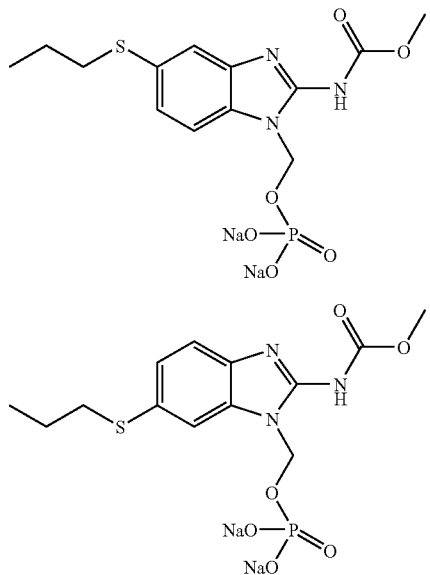

The compounds 14 and 15 were synthesised by using the synthetic sequence described in Example 1. In this case, however, it was more appropriate during the first step to add a solution of the sodium salt of (5-propylsulfanyl-1H)-benzoimidazol-2-yl)-carbamic acid methyl ester in N-methylpyrrolidone to a solution of phosphoric acid di-tert-butyl ester chloromethyl ester in dimethylformamide. 1-Phosphonooxymethyl-5-propylsulfanyl-1(H)-benzoimidazol-2-yl)-carbamic acid methyl ester di-sodium salt 14 and 1-phosphonooxymethyl-6-propylsulfanyl-1(H)-benzoimidazol-2-yl)-carbamic acid methyl ester di-sodium salt 15. $^1$H-NMR (D$_2$O) δ 7.53-7.22 (m, 6H), 5.58 (s, 4H), 3.70 (s, 6H), 2.91-2.83 (m, 4H), 1.56-1.49 (m, 4H), 0.90-0.85 (m, 6H); $^{31}$P-NMR (D$_2$O) δ 2.71 (s).

Example 6

(5-Butyl-1-phosphonooxymethyl-1(H)-benzoimidazol-2-yl)-carbamic acid methyl ester di-sodium salt 16 and (6-butyl-1-phosphonooxymethyl-1(H)-benzoimidazol-2-yl)-carbamic acid methyl ester di-sodium salt 17

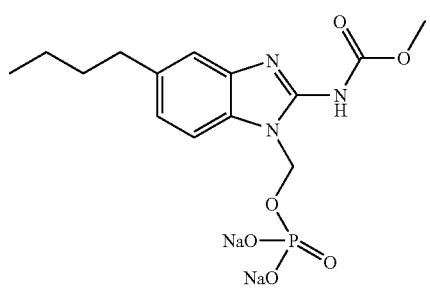

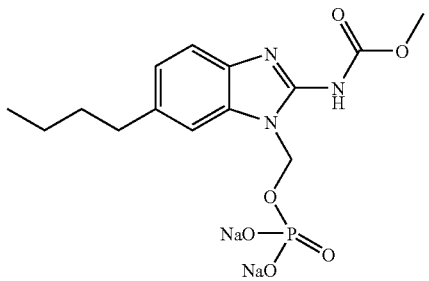

The compounds 16 and 17 were synthesised by using the synthetic sequence described in Example 1. (5-Butyl-1-phosphonooxymethyl-1(H)-benzoimidazol-2-yl)-carbamic acid methyl ester di-sodium salt 16 and (6-butyl-1-phosphonooxymethyl-1(H)-benzoimidazol-2-yl)-carbamic acid methyl ester di-sodium salt 17. $^1$H-NMR (D$_2$O) δ 7.36-7.00 (m, 6H), 5.51 (d, 4H), 3.62 (s, 6H), 2.55 (q, 4H), 1.50-1.43 (m, 4H), 1.22-1.13 (m, 4H), 0.78-0.74 (m, 6H); $^{31}$P-NMR (D$_2$O) δ 2.50 (s).

Example 7

(5-Benzenesulfinyl-1-phosphonooxymethyl-1(H)-benzoimidazol-2-yl)-carbamic acid methyl ester di-sodium salt 18 and (6-benzenesulfinyl-1-phosphonooxymethyl-1(H)-benzoimidazol-2-yl)-carbamic acid methyl ester di-sodium salt 19

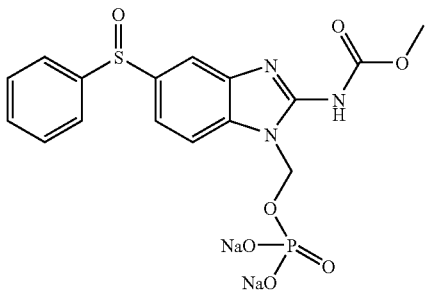

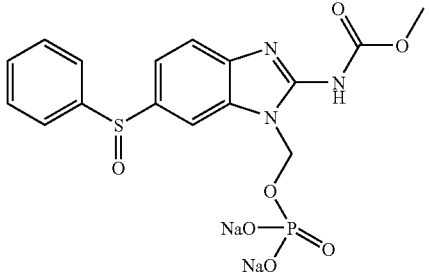

The compounds 18 and 19 were synthesised by using the synthetic sequence described in Example 1. (5-Benzenesulfinyl-1-phosphonooxymethyl-1(H)-benzoimidazol-2-yl)-carbamic acid methyl ester di-sodium salt 18 and (6-benzenesulfinyl-1-phosphonooxymethyl-1(H)-benzoimidazol-2-yl)- carbamic acid methyl ester di-sodium salt 19. $^1$H-NMR (D$_2$O) δ 7.74-7.43 (m, 16H), 5.63 (d, 4H), 3.71 (m, 6H); $^{31}$P-NMR (D$_2$O) δ 3.25 (s).

The utility of the compounds as anthelmintics can, for example, be assessed by the following techniques:

Example 8

Activity against *Ascaridia galli* (Intestinal Roundworm of Chicken) and *Oesophagostomum dentatum* (Nodular Worm of Swine)

Anthelmintic effects of the compounds of the present invention were tested in vitro using gut welling larval stages of two parasitic nematode species: *Ascaridia galli* (intestinal roundworm of chicken), larval stage 3 (L3), and *Oesophagostomum dentatum* (nodular worm of swine), larval stages 3 and 4 (L3; LA).

Principle of the assays: Various concentrations of compounds were incubated in 96 well microtiter plates, in which parasites were then distributed at 20 larvae per well. The anthelmintic effects were classified at day 5 by microscopic examination assessing mortality, damage, motility, progression of development and neutral red uptake by the larvae in comparison to a DMSO-control and the standard anthelmintics fenbendazole. The anthelmintic effects were defined by the minimum effective concentration (MEC) as reflected in table 1.

TABLE 1 anthelmintic effects defined by the minimum effective concentration (MEC)

| Compounds | Minimum effective concentrations (µM) | | |
|---|---|---|---|
| | *A. galli* (L3) | *O. dentatum* (L3) | *O. dentatum* (L4) |
| 4 and 5 (as a 1:1 mixture) | 0.050 | 0.050 | 0.050 |
| | 0.050 | 0.050 | 0.050 |
| | 0.025 | 0.050 | 0.050 |
| | 0.050 | 0.050 | 0.050 |
| fenbendazole | 0.050 | 1.000 | 0.025 |

Example 9

Evaluation of the Anthelmintic Efficacy of (5- and 6-phenylsulfanyl-1-phosphonooxymethyl-1(H)-benzoimidazol-2-yl)-carbamic acid methyl esters in Chicken Experimentally Infected with *Ascaridia galli*

This study was designed to assess the efficacy of (5- and 6-phenylsulfanyl-1-phosphonooxymethyl-1(H)-benzoimidazol-2-yl)-carbamic acid methyl esters (further referred to as "Compound A"), in comparison with fenbendazole mixed in feed and a market formulation of fenbendazole (Panacur® Suspension 2.5% ad us. vet.) against *A. galli* in experimentally infected chicken.

Chickens were experimentally infected orally (per gavage) with 150 larvae containing eggs from *A. galli*. A total of 60 chickens were grouped in boxes of 5 chickens and sorted into 4 treatment groups (A-D) consisting of 15 chickens each. The animals were fed a complete diet for broiler chicks, and had free access to drinking water. Group A was treated with Compound A, group B was treated with Panacur® Suspension 2.5%, and group C was fed complete diet medicated with fenbendazole. Group D served as an untreated control and was applied deionised water without drug. Details of the treatment groups are listed in Table 1.

Preparation of Treatment Formulations

Compound A was weighed into 50 mL screw cap tubes and dissolved in aqueous NaHCO$_3$. The Panacur® Suspension 2.5% was transferred into 50 mL screw cap tubes and diluted with deionised water. Fenbendazole was mixed with the complete diet for broiler chicks.

Dosage and Application

Groups A, B and D were dosed orally by gavage divided into 4 single doses daily on 5 consecutive days, group C was fed medicated feed. The doses given per gavage were calculated based on the mean feed intake measured under the assumption that the feed would have been medicated.

Details of dosing and administration are listed in Table 2.

TABLE 2

Dosing and administration details

| Group | Box | Compound | Formulation | Dosage | Administration |
|---|---|---|---|---|---|
| A | 1 | Compound A | aqueous NaHCO$_3$ | 100 ppm | 0.5 ml per gavage, 4 times daily |
| | 2 | | | | |
| | 3 | | | | |
| B | 4 | Panacur ® Suspension 2.5% | Deionised water | 60 ppm | |
| | 5 | | | | |
| | 6 | | | | |
| C | 7 | fenbendazole | Medicated feed | 100 ppm | In feed ad libitum |
| | 8 | | | | |
| | 9 | | | | |
| D | 10 | — | Deionised water | — | 0.5 ml per gavage, 4 times daily |
| | 11 | | | | |
| | 12 | | | | |

From D0 (first treatment) until D8 (necropsy) the excreted worms were collected once or twice daily and counted. The animals were euthanised 4 days after the last treatment, and the gastro-intestinal tract was removed and opened (except caeca). The adult worms present in the intestine were counted.

The result of the treatment was a 100% reduction in worm numbers in all treated groups (A-C) compared to the control group (D).

Example 10

Evaluation of the Anthelmintic Efficacy of (5- and 6-phenylsulfanyl-1-phosphonooxymethyl-1(H)-benzoimidazol-2-yl)-carbamic acid methyl esters in Birds Experimentally Infected with *Haemonchus contortus*

This study was designed to compare the anthelmintic efficacy of (5- and 6-phenylsulfanyl-1-phosphonooxymethyl-1 (H)-benzoimidazol-2-yl)-carbamic acid methyl esters (further referred to as "Compound A") and fenbendazole against a stomach strongylid nematode (*Haemonchus contortus*) in birds (*Meriones unguiculatus*) after intraperitoneal (IP), subcutaneous (SC) and oral (PO) administration. The compounds were tested at doses of 3 mg/kg bodyweight (BW), 1 mg/kg BW and 0.3 mg/kg BW.

The animals were orally infected with $L_3$-larvae of *H. contortus*. On D 10 post infectionem (PI) animals were treated once IP, SC or PO with the test compounds in 10% DMF/90% water at doses of 3.0 mg/kg BW, 1.0 mg/kg BW or 0.3 mg/kg BW. Three days after treatment animals were necropsied and larvae burden in stomachs was determined. Efficacy was defined as the reduction of the mean larvae count (geometric mean) in the treatment groups in comparison to the control group. The dose-response relationship was investigated by calculating Pearson's coefficient of correlation.

For fenbendazole and a dose of 3 mg/kg BW a reduction of larvae numbers between 95.10% (SC administration) and 100.00% (IP administration) was observed. For groups dosed with 1 mg/kg BW the reduction was between 78.05% (PO administration) and 89.33% (IP administration). For groups dosed with 0.3 mg/kg BW the reduction was between 80.63% (IP administration) and 91.73% (PO administration).

For Compound A and a dose of 3 mg/kg BW (1.8 mg/kg BW fenbendazole equivalent) a reduction of larvae numbers between 90.81% (PO administration) and 94.84% (SC administration) was observed. For groups dosed with 1 mg/kg BW (0.6 mg/kg BW fenbendazole equivalent) the reduction was between 87.61% (SC administration) and 90.65% (IP administration). For groups dosed with 0.3 mg/kg BW (0.2 mg/kg SW fenbendazole equivalent) the reduction was between 47.40% (SC administration) and 87.00% (PO administration). All reductions of larvae numbers of the treatment groups were significantly different in comparison to the control group.

The result as described above are depicted in Table 3.

TABLE 3

Efficacy of fenbendazole and compound A on the number of larvae of *H. contortus* in comparison with the untreated control group

| Route of administration | Fenbendazole equivalent [mg/kg] | | Reduction worm number (%) | |
|---|---|---|---|---|
| | Fenbendazole | Compound A | Fenbendazole | Compound A |
| IP | 3.0 | 1.8 | 100.00 | 93.81 |
| SC | | | 95.10 | 94.84 |
| PO | | | 96.49 | 90.81 |
| IP | 1.0 | 0.6 | 89.33 | 90.65 |
| SC | | | 89.16 | 87.61 |
| PO | | | 78.05 | 88.62 |
| IP | 0.3 | 0.2 | 80.63 | 65.02 |
| SC | | | 88.36 | 47.40 |
| PO | | | 91.73 | 87.00 |
| IP/SC/PO | — | — | — | — |

Treatment with compound A had the same efficacy as treatment with fenbendazole and the comparison of the larvae counts between the different fenbendazole equivalents showed a high correlation with a coefficient of correlation of $R=-0.7622$. Dose-dependency and dose-correlation could be proven for both compounds.

Example 11

Evaluation of the Anthelmintic Efficacy of (5- and 6-phenylsulfanyl-1-phosphonooxymethyl-1(H)-benzoimidazol-2-yl)-carbamic acid methyl esters in Birds Experimentally Infected with *Trichostrongylus axei* and *T. colubriformis*

This study was designed to compare the anthelmintic efficacy of (5- and 6-phenyl sulfanyl-1-phosphonooxymethyl-1 (H)-benzoimidazol-2-yl)-carbamic acid methyl esters (further referred to as "Compound A") and fenbendazole against stomach and intestinal strongylid nematodes (*T. axei* and *T. colubriformis*) in birds (*Meriones unguiculatus*) after intraperitoneal (IP), subcutaneous (SC) and oral (PO) administration. The compounds were tested at doses of 3 mg/kg bodyweight (BW), 1 mg/kg BW and 0.3 mg/kg BW.

The animals were orally infected $L_3$-larvae of each *T. axei* and *T. colubriformis*. On D 19 post infectionem (PI) animals were treated once IP, SC or PO with the test compounds in 10% DMF/90% water a dose of 3 mg/kg BW, 1 mg/kg BW or 0.3 mg/kg BW. Three days after treatment animals were necropsied and worm burden in stomach and small intestine was determined. Efficacy was defined as the reduction of the mean worm count (geometric mean) in the treatment groups in comparison to the control group. The dose-response relationship was investigated by calculating Pearson's coefficient of correlation.

For fenbendazole and a dose of 3 mg/kg BW a reduction of worm numbers of 100% was observed for all three administrations and both worm species and was significantly different in comparison to the control group ($p=0.0011$). For groups dosed with 1 mg/kg BW the reduction was between 80.94% (IP administration; $p=0.0422$) and 88.80% (PO administration; $p=0.0162$) for the infection with *T. axei*. For *T. colubriformis* the reduction of worm numbers was between 80.04% (IP administration; $p=0.0173$ and PO administration; $p=0.0563$) and 81.10% (SC administration; $p=0.0097$). For groups dosed with 0.3 mg/kg BW the reduction was 82.15% for SC administration ($p=0.0162$) for the infection with *T. axei* and no reduction of worm numbers could be observed for the other administrations (IP administration: −283.85%; $p=$not calculable and PO administration: −115.44%; $p=$not calculable). For *T. colubriformis* the reduction of worm numbers was between 43.18% (SC administration; $p=0.2543$) and 79.33% (IP administration; $p=0.0162$).

For compound A and a dose of 3 mg/kg BW (1.8 mg/kg BW fenbendazole equivalent a reduction of worm numbers between 98.00% (PO administration; $p=0.0011$) and 100% (IP and SC administration; $p=0.0011$) was observed for infection with *T. axei*. For infection with *T. colubriformis* the reduction of worm numbers was between 85.70% (SC administration; $p=0.0108$) and 100.00% (PO administration; $p=0.0011$). For groups dosed with 1 mg/kg BW (0.6 mg/kg BW fenbendazole equivalent) the reduction was between 82.98% (SC administration; $p=0.0108$) and 96.71% (PO administration; $p=0.0022$) for the infection with *T. axei*. For *T. colubriformis* the reduction of worm numbers was between 28.18% (IP administration; $p=0.3019$) and 68.61% (SC administration; $p=0.0682$). For groups dosed with 0.3 mg/kg BW (0.2 mg/kg BW fenbendazole equivalent the reduction was 69.66% for IP administration ($p=0.0530$) and 59.20% for PO administration ($p=0.1407$) for the infection with *T. axei* and no reduction of worm numbers could be observed for SC administration (43.64%; $p=$not calculable). For *T. colubriformis* no reduction of worm numbers could be observed for IP administration (−50.17%; $p=$not calculable), SC administration (−106.50%; $p=$not calculable) and for PO administration (−3.71%; $p=0.4740$).

The result as described above are depicted in Table 4.

TABLE 4

Efficacy of fenbendazole and compound A on the number of worms of *T. axei* and *T. colubriformis* in comparison with the untreated control group

| Worm species | Route of administration | Fenbendazole equivalent [mg/kg] | | Reduction worm number (%) | |
|---|---|---|---|---|---|
| | | Fenbendazole | Compound A | Fenbendazole | Compound A |
| *T. axei* | IP | 3.0 | 1.8 | 100.00 | 100.00 |
| | SC | | | 100.00 | 100.00 |
| | PO | | | 100.00 | 98.00 |
| | IP | 1.0 | 0.6 | 80.94 | 83.98 |
| | SC | | | 82.15 | 82.98 |
| | PO | | | 88.80 | 96.71 |
| | IP | 0.3 | 0.2 | −283.85 | 69.66 |
| | SC | | | 82.15 | −43.64 |
| | PO | | | −115.44 | 59.20 |
| | IP/SC/PO | — | — | — | — |
| *T. colubriformis* | IP | 3.0 | 1.8 | 100.00 | 93.26 |
| | SC | | | 100.00 | 85.70 |
| | PO | | | 100.00 | 100.00 |
| | IP | 1.0 | 0.6 | 80.04 | 28.18 |
| | SC | | | 81.10 | 68.61 |
| | PO | | | 80.04 | 37.27 |
| | IP | 0.3 | 0.2 | 79.33 | −50.17 |
| | SC | | | 43.18 | −106.50 |
| | PO | | | 68.75 | −3.71 |
| | IP/SC/PO | — | — | — | — |

Treatment with compound A had the same efficacy as treatment with fenbendazole and the comparison of the worm counts between the different fenbendazole equivalents showed a high correlation with a coefficient of correlation of R=−0.8146 for *T. axei* and R=−0.9161 for *T. colubriformis*. Dose-dependency and dose-correlation could be proven for both compounds.

The invention claimed is:

1. A compound of Formula I:

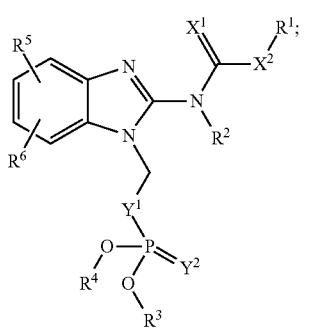

(I)

$X^1$ and $X^2$ are independently O or S, wherein at least one of $X^1$ and $X^2$ is O;
$Y^1$ and $Y^2$ are independently O or S, wherein at least one of $Y^1$ and $Y^2$ is O;
$R^1$ is alkyl of 1-4 carbon atoms;
$R^2$, $R^3$, and $R^4$ are independently hydrogen or a cation;
$R^5$ and $R^6$ are independently hydrogen, halogen, alkyl of 1-8 carbon atoms, —$OR^7$, —$SR^8$, —CO—$R^9$, —$OSO_2$—Ar, or —$S(O)R^{10}$;
$R^7$ is alkyl of 1-8 carbon atoms;
$R^8$ is alkyl of 1-8 carbon atoms or aryl;
$R^9$ is alkyl of 1-8 carbon atoms, cycloalkyl of 3-6 carbon atoms, or aryl;
Ar is aryl; and
$R^{10}$ is alkyl of 1-8 carbon atoms or aryl.

2. A compound according to claim 1, wherein $X^1$ and $X^2$ are both O.

3. A compound according to claim 1, wherein $Y^1$ and $Y^2$ are both O.

4. A compound according to claim 1, wherein $X^1$, $X^2$, $Y^1$, and $Y^2$ are O.

5. A compound according to claim 1, wherein:
$R^2$ is H, and $R^3$ and $R^4$ are sodium.

6. A compound according to claim 1, wherein $R^1$ is methyl.

7. A compound according to claim 1, wherein:
$R^5$ is H, and
$R^6$ is n-butyl.

8. A compound according to claim 1, wherein:
$R^5$ is H,
$R^6$ is —$OR^7$, and
$R^7$ is n-propyl.

9. A compound according to claim 1, wherein:
$R^5$ is H,
$R^6$ is —$SR^8$, and
$R^8$ is n-propyl.

10. A compound according to claim 1, wherein:
$R^5$ is H,
$R^6$ is —$SR^8$, and
$R^8$ is phenyl.

11. A compound according to claim 1, wherein:
$R^5$ is H,
$R^6$ is —CO—$R^9$, and
$R^9$ is phenyl.

12. A compound according to claim 1, wherein:
$R^5$ is H,
$R^6$ is —$OSO_2$—Ar, and
Ar is phenyl substituted in position 4 by a fluorine atom.

13. A compound according to claim 1, wherein:
$R^5$ is H,
$R^6$ is —$S(O)R^{10}$, and
$R^{10}$ is n-propyl.

14. A compound according to claim 6, wherein $R^6$ is attached to either the 5 position on the benzimidazole nucleus.

15. A pharmaceutical composition, wherein the composition comprises:

a compound according to claim 1, and a pharmaceutically acceptable carrier.

16. A method of treating an animal against a parasite, wherein the method comprises administering a compound of claim 1 to the animal.

17. A method of treating an animal against a helminth, wherein the method comprises administering a compound of claim 1 to the animal.

18. The compound of claim 1, wherein $R^2$, $R^3$, and $R^4$ are sodium.

19. The compound of claim 1, wherein $R^5$ is H, and wherein $R^6$ is —CO—$R^9$ and $R^9$ is phenyl, substituted in position 4 by a fluorine atom.

20. The compound of claim 1, wherein $R^5$ is H, and wherein $R^6$ is —S(O)$R^{10}$ and $R^{10}$ is phenyl.

21. The compound of claim 1, wherein $R^6$ is attached to the 6-position on the benzimidazole nucleus.

22. The method according to claim 16, wherein the compound is administered to the animal by providing the animal with drinking water comprising the compound.

23. The method according to claim 17, wherein the compound is administered to the animal by providing the animal with drinking water comprising the compound.

24. The pharmaceutical composition of claim 15, wherein the pharmaceutically acceptable carrier is a liquid diluent.

* * * * *

UNITED STATES PATENT AND TRADEMARK OFFICE
CERTIFICATE OF CORRECTION

PATENT NO. : 7,893,271 B2
APPLICATION NO. : 11/997057
DATED : February 22, 2011
INVENTOR(S) : Christophe Pierre Alain Chassaing It is certified that error appears in the above-identified patent and that said Letters Patent is hereby corrected as shown below:

In the claims:
CLAIM 14,   COLUMN 23,   LINE 2,   change "either the" to --the--

Signed and Sealed this
Seventeenth Day of May, 2011

David J. Kappos
*Director of the United States Patent and Trademark Office*